US011957927B1

(12) United States Patent
Fernandes

(10) Patent No.: US 11,957,927 B1
(45) Date of Patent: Apr. 16, 2024

(54) POLARIZED MULTI-LENS APPARATUS FOR SELECTIVE SCOTOMA SIMULATION

(71) Applicant: Nayson Luis Fernandes, Saratoga, CA (US)

(72) Inventor: Nayson Luis Fernandes, Saratoga, CA (US)

(*) Notice: Subject to any disclaimer, the term of this patent is extended or adjusted under 35 U.S.C. 154(b) by 358 days.

(21) Appl. No.: 16/737,906

(22) Filed: Jan. 9, 2020

Related U.S. Application Data

(60) Provisional application No. 62/790,439, filed on Jan. 9, 2019.

(51) Int. Cl.
| | | |
|---|---|---|
| *A61N 5/073* | (2006.01) | |
| *A61B 3/00* | (2006.01) | |
| *A61B 3/024* | (2006.01) | |
| *A61N 5/06* | (2006.01) | |
| *G02C 7/04* | (2006.01) | |
| *G02C 7/08* | (2006.01) | |
| *G02C 7/12* | (2006.01) | |

(52) U.S. Cl.
CPC .............. *A61N 5/06* (2013.01); *A61B 3/0008* (2013.01); *A61B 3/024* (2013.01); *G02C 7/048* (2013.01); *G02C 7/086* (2013.01); *G02C 7/12* (2013.01); *A61B 2503/12* (2013.01); *A61N 2005/0648* (2013.01); *A61N 2005/0657* (2013.01); *A61N 2005/073* (2013.01)

(58) Field of Classification Search
CPC ........ A61N 5/06; A61B 3/0008; A61B 3/024; G02C 7/048; G02C 7/086; G02C 7/12

USPC .......................................................... 351/215
See application file for complete search history.

(56) References Cited

U.S. PATENT DOCUMENTS

| | | | | |
|---|---|---|---|---|
| 4,818,091 A | * | 4/1989 | Sadun ...................... | G02C 7/12 |
| | | | | 351/49 |
| 5,050,982 A | * | 9/1991 | Meissner ................ | A61F 9/022 |
| | | | | 351/203 |
| 5,139,323 A | * | 8/1992 | Schillo ................... | G02C 5/001 |
| | | | | 351/203 |

(Continued)

FOREIGN PATENT DOCUMENTS

| | | | | |
|---|---|---|---|---|
| EP | 3502768 A1 | * | 6/2019 | ............. G02C 7/104 |
| JP | 2000325310 A | * | 11/2000 | |

(Continued)

*Primary Examiner* — James R Greece

(57) ABSTRACT

Selective visual field restriction or stimulation during ocular movement is a challenging task that holds promise for basic research and for simulating, measuring, monitoring, and treating psychological, neurological, and ophthalmological conditions. This invention discloses an optical apparatus and method that can restrict visual information from reaching selected areas of one or both retina of a human user during free ocular scanning, using a combination of (1) polarized contact lenses that have at least two areas that each linearly polarize light in planes orthogonal to one another, (2) spectacle lenses that linearly polarize light uniformly across the lenses, and (3) spectacle frames that allow said spectacle lenses to rotate. Depending upon the rotational degree difference between the planes of polarization between the spectacle lenses and each area of the contact lenses, light can be restricted from reaching certain areas of the retina of one or both eyes of a human user.

5 Claims, 4 Drawing Sheets

(56) References Cited

U.S. PATENT DOCUMENTS

2008/0151175 A1* 6/2008 Gross .................... G02C 7/105
　　　　　　　　　　　　　　　　　　　　　　　　351/45
2010/0283957 A1* 11/2010 Matera .................... G02B 5/23
　　　　　　　　　　　　　　　　　　　　　　　　351/49

FOREIGN PATENT DOCUMENTS

WO　　WO-2008078320 A2 *　7/2008　............... G02C 7/06
WO　　WO-2009019451 A1 *　2/2009　............... G02C 7/04

* cited by examiner

POLARIZED MULTI-LENS APPARATUS FOR SELECTIVE SCOTOMA SIMULATION

CROSS-REFERENCE TO RELATED APPLICATIONS

This application is associated with the U.S. Provisional Patent Application No. 62,790,439 filed Jan. 9, 2019.

STATEMENT REGARDING FEDERALLY SPONSORED RESEARCH OR DEVELOPMENT

Not applicable

SEQUENCE LISTING, TABLE, OR COMPUTER PROGRAM LISTING APPENDIX

Not applicable

FIELD OF INVENTION

This invention pertains to a means for simulating visual field scotomas monocularly or binocularly during free ocular scanning for research, diagnostic, prognostic, therapeutic, and commercial purposes.

BACKGROUND OF THE INVENTION

Visual processing in humans is known to be lateralized around the vertical meridian of the visual field; visual hemi-field input from each eye traverses through nerve fibers in the optic nerves, chiasm, and tracts to processing centers in the cerebral hemisphere contralateral to the side of visual input. Thus, left visual hemi-field stimuli are thought to be first processed in the right visual cortex and right visual hemi-field stimuli in the left visual cortex before interhemispheric transfer of visual information across the corpus callosum. Methods using selective hemi-field restriction or stimulation have been developed to study hemispheric specialization and interhemispheric interactions in both normal and clinical populations.

Prior to 1970 tachistoscopic methods were the primary means for selectively stimulating visual hemi-fields. The duration of stimuli presentation in this method must be very short—less than the time required for human eyes to make reflexive saccades towards the stimuli. Longer presentation times allow saccades and thus both visual hemi-fields access to the stimuli. Though still used widely in psychology laboratories today, tachistoscopic experimentation has significant limitations, including unnatural millisecond range visual stimuli presentations and visual fixation on a crosshair without permitting free ocular scanning. Tachistoscopic techniques also require eye-movement control measures, such as eye tracking, to ensure that the participant is indeed fixating on the crosshair.

In the early 1970s Dr. Eran Zaidel, under the guidance of Dr. Roger Sperry at the California Institute of Technology, developed a novel technique to present visual stimuli selectively to the left or right cerebral hemisphere in complete corpus callosotomy patients by utilizing a contact lens apparatus called the Z-lens. The Z-lens stabilized a stimuli presentation screen on a contact lens by using a collimator affixed with an occluding cap, which allowed prolonged stimulation of a select visual hemi-field during free ocular scanning. Though a significant improvement over tachistoscopic methodologies, the Z-lens is limited by its design for monocular use. Furthermore, the Z-lens requires suction to the eye to prevent rotation and slippage of the contact lens, and additional lubrication of the eye, because blinking is not permissible with the collimator in place. Suction limited the time that the Z-lens could be used to approximately 30 minutes; use beyond 30 minutes risked damage to the avascular cornea that normally relies on direct exposure to air for oxygenation. Nevertheless, experimentation using this apparatus contributed to a significant body of scientific literature that strongly shapes humanity's understanding of the visual system and cerebral hemispheres.

Several newer techniques are available for selective scotoma simulation, including partially occluded glasses. Examples of partially occluded glasses include U.S. Pat. No. 4,582,401 by Mary M. Grindle, titled "Visual field and lens occluder for eyeglasses" and U.S. Pat. No. 5,963,294 by Fredric Schiffer, titled "Method for using therapeutic glasses for stimulating a change in the psychological state of a subject". Each of these patents allows for binocular use—an advantage over the Z-lens technique. However, partially or hemi-occluded glasses do not track the eyes and allow both the left and right visual hemi-fields of each eye access to the non-occluded portion of the glasses during eye movements.

Contact lenses have also been developed for selective scotoma stimulation and include U.S. Pat. No. 6,062,687 by Gunilla Lofgren-Nisser, titled "Partially occluded contact lens for treating visual and/or brain disorder; U.S. Pat. No. 5,570,144 by Gunilla Lofgren-Nisser, titled "Field restrictive contact lens"; U.S. Pat. No. 6,595,636 by Avram J. Zoltem, titled "Occluded contact lens with peripheral vision functionality"; and U.S. Pat. No. 5,886,769 by Avram J. Zoltem, titled "Method of training and rehabilitating brain function using hemi-lenses". Each of these partially occluded contact lens devices appears advantageous over glasses because the occluded portion of the lenses track the movements of the eyes. However, these techniques were described in the public domain during the development of the Z-lens, which occurred at least a decade prior to the publication dates of the aforementioned patents, and were not used during the study of corpus callosotomy patients due to light diffraction around the edges of the occluded area. This issue was addressed in the Z-lens by occluding visual hemi-fields at the plane of fixation, rather than on the surface of the eye. Diffraction on the surface of the eye may be minimizable if the material used to occlude a portion of visual field is composed of the same material as the non-occluded areas.

There is a separate body of literature that describes contact lenses with positional stability. This feature is necessary to keep the vertical meridian of a hemi-occluded contact lens upright and centered along the vertical meridian of the cornea. An example is U.S. Pat. No. 3,431,327 by George F. Tsuetaki titled "Method of making a bifocal contact lens with an embedded metal weight", which describes increased weight at the bottom of a bi-focal contact lens. U.S. Pat. No. 6,062,687 describes using such a weight-based technique on a partially occluded contact lens, but again, a partially occluded contact lens by itself does not faithfully occlude select portions of the retina due to diffraction. Slippage is another factor that needs to be addressed while using contact lenses for scotoma simulations. If a lens slips off the midline of the cornea then the desired hemi-field occlusion is not achievable. U.S. Pat. No. 3,495,899A by Henri Biri, titled "Scleral contact lenses", addresses this through a scleral contact lens that conforms to the topographical change that occurs at the corneal Embus of the eye as cornea transitions to sclera. A combination of scleral and bottom-weighted contact lenses achieves the positional stability necessary when using a contact lens during visual hemi-field restriction or stimulation, without requiring burdensome or dangerous techniques such as suction of a contact lens to the eye.

Another separate body of literature describes lens polarization techniques that can be embedded in lenses. Combining multiple plane polarized lenses that each polarize light in a different plane can restrict light from passing through them. This technique is the basis of liquid crystal displays and has been used in wearable lenses. An example includes U.S. Pat. No. 5,142,411A by Werner J. Fiala, titled "Multifocal birefringent lens system". However, neither this patent nor others in this field have been used in wearable lenses to simulate visual scotomas.

Missing from these bodies of scientific work is a method that allows accurate, ergonomic, and comfortable visual hemi-field restriction or stimulation during prolonged and unrestricted binocular movement. Furthermore, as of the filing of this patent application, there are no published patents or scientific literature that combine contact and spectacle lenses with polarization techniques to achieve visual hemi-field modulation.

BRIEF SUMMARY OF THE INVENTION

A primary object of the present invention is to create an optical apparatus that allows scotoma simulation, including simulation of homonymous hemianopia, bitemporal hemianopia, or homonymous quadrantanopia, among other conditions, for basic and clinical research, or for diagnostic, prognostic, and therapeutic applications.

A preferred embodiment of the apparatus described in this present invention comprises contact lenses, spectacle lenses, and a spectacle frame. The contact lenses are rotationally and positionally stabilized, such that the contact lenses move in sync with eye movements and do not rotate. Each contact lens is split at the vertical meridian with one visual hemi-field built of material that linearly polarizes light in the horizontal plane and the other visual hemi-field built of the same material, but with linear polarization achieved in the vertical plane. The spectacle lenses linearly polarize light into a single plane, uniformly across the lenses, and can be rotated within the spectacle frame. This rotational feature allows ergonomic control over the plane of polarization of the spectacle lenses. When a user wears the contact lenses with the spectacle lenses and frame in a lit environment, each visual hemi-field can be selectively occluded by rotating the spectacle lenses 90 degrees. For example, if the spectacle lenses are oriented within their frame to linearly polarize light in the vertical plane, light will only enter the contact lenses through the half of each contact lens that also polarizes light in the vertical plane. Rotating the spectacle lenses 90 degrees in either direction, to the horizontal plane polarization position, would then selectively allow light to enter the contact lenses through the contralateral halves that are horizontally plane polarized.

This embodiment of the invention is advantageous over prior art by allowing scotoma simulation during prolonged binocular free-scanning when worn on a human user. There is no need for eye suction or additional eye lubrication because there is no obstruction to blinking. In addition, the material used across the contact lenses is made of the same material, which diminishes if not removes diffraction issues that previous partially-occluded contact lenses did not address. Finally, the rotatable spectacle lenses allow for quick and easy modulation of various visual scotomas.

DETAILED DESCRIPTION OF THE EMBODIMENT

Figure 1:
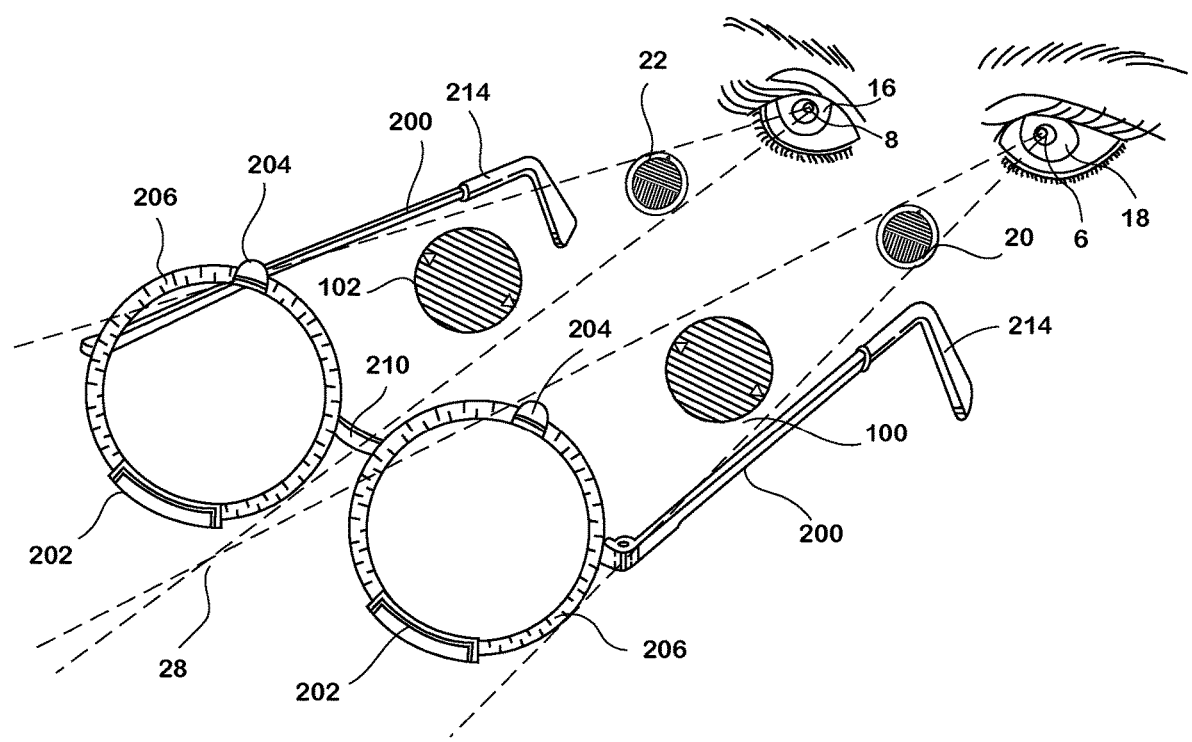
FIG. 1 shows an exploded perspective view of all components of one embodiment of the invention, which includes a spectacle frame, spectacle lenses, and contact lenses as they would fit in relation to the eyes of a human user.

FIG. 1 depicts an exploded view of all components of a preferred embodiment of this invention in relation to the left eye 18 and right eye 16 of a human user, and to their lines of sight 28 originating from their left pupil 6 and right pupil 8. A left contact lens 20 and a right contact lens 22 are depicted in FIG. 1 to demonstrate their relationship to other parts of this invention, and are described in greater detail in FIGS. 3A, 3B, and 3C. These contact lenses are placed on the eyes of a human user in order to use this invention. Spectacle frames 200 are also placed on said human user and hold a circular plane polarized left spectacle lens 100 and circular plane polarized right spectacle lens 102. The spectacle lenses are held in place within the circular rims of the spectacle frames by a bottom mounting bracket 202 and a top mounting bracket 204 in a loose manner that allows rotation of the spectacle lenses. Angle markings 206 on the rims of the glasses allow a user to know the degree to which the spectacle lenses are rotated. The spectacle frames also consist of a nasal bridge 210 and temple tips 214 that allow for comfortable and stable positioning of the spectacle frame on said human wearer.

Figure 2:
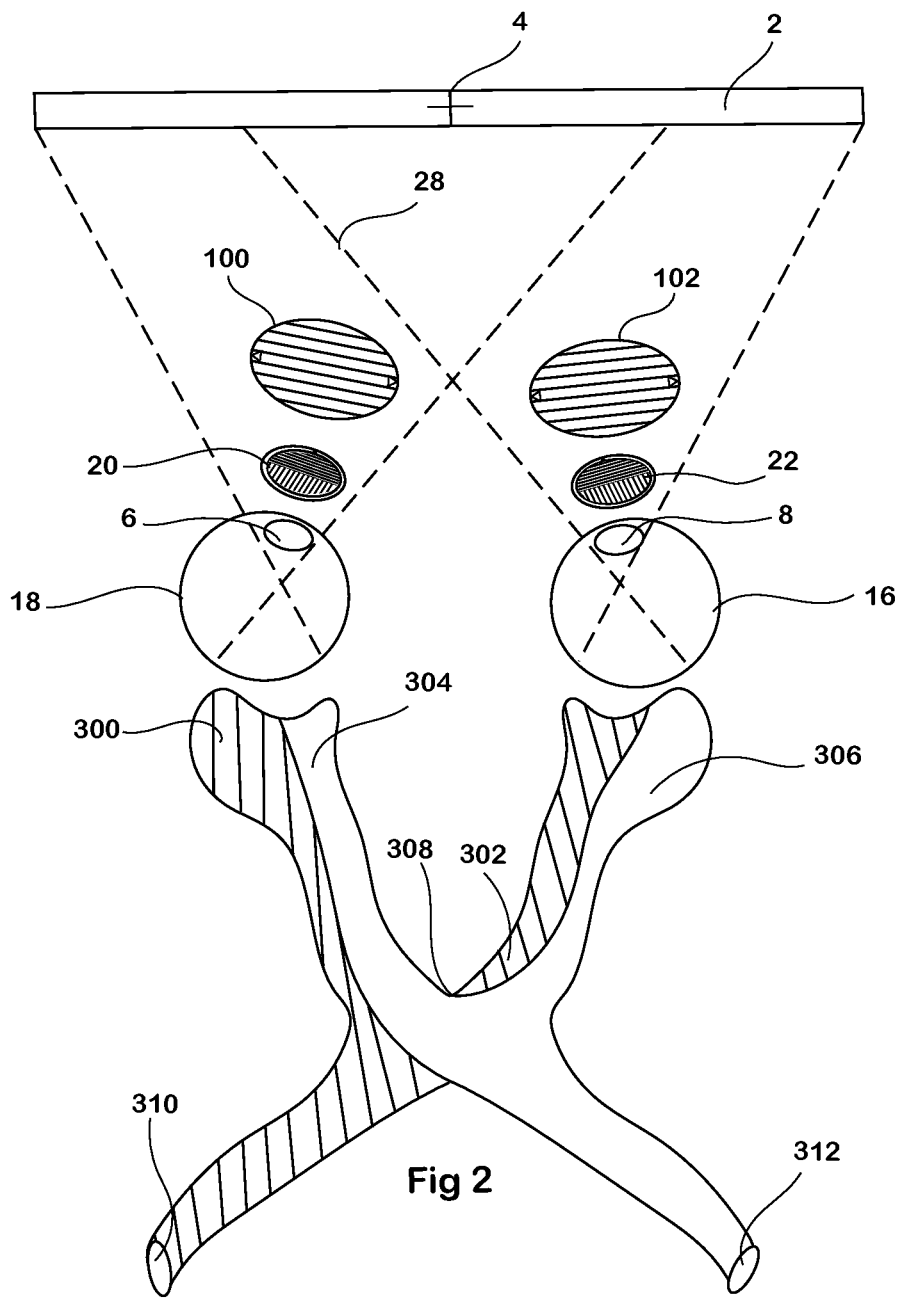
FIG. 2 shows the flow of visual information from a presentation screen through spectacle lenses, contact lenses, human eyes, and ultimately optic nerves, chiasm, and tracts.

FIG. 2 depicts the positioning of the optical components of the preferred embodiment of this invention and how visual information traverses through lateralized visual processing centers in the brain. A left spectacle lens 100 and a right spectacle lens 102 are positioned in front of a left contact lens 20 and a right contact lens 22. The left contact lens 22 is placed over the left pupil 6 of the left eye 18 and the right contact lens 22 is placed over the right pupil 8 of the right eye 16 of a human user. The human user is looking at a fixation crosshair 4 on a presentation screen 2, with dashed lines depicting lines of sight 28. Visual information on the left of the fixation crosshair 4 stimulates the right hemi-retina at the posterior aspect of each eye. From the left eye 18 Left Visual Field (LVF) information traverses through nasal nerve fibers of the left optic nerve 304 and in the right eye 16 this LVF information traverses through temporal nerve fibers of the right optic nerve 306, before joining at the optic chiasm 308 and continuing together through right hemisphere optic tracts 310. Similarly, Right Visual Field (RVF) information stimulates the left hemiretina at the posterior aspect of each eye. From the left eye 18 this RVF information traverses through temporal nerve fibers of the left optic nerve 300 and from the right eye 16 this RVF information traverses through nasal nerve fibers of the right optic nerve 302, before joining at the optic chiasm 308 and continuing together through left hemisphere optic tracts 312.

Figure 3A:
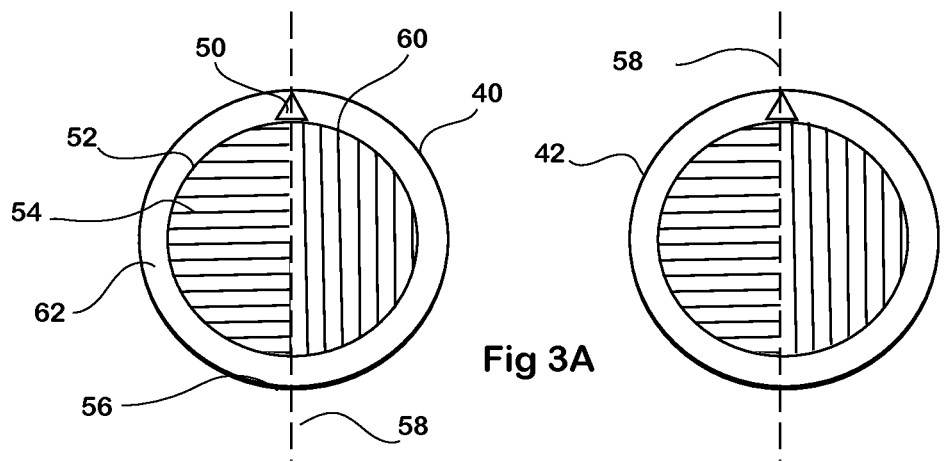
FIGS. 3A, 3B, and 3C shows multiple embodiments of the contact lenses portion of this invention in more detail, as viewed through the eyes of a human wearer, in configurations that can allow for simulation of left or right homonymous hemianopia, superior or inferior homonymous hemianopia, and homonymous quadrantanopia, respectively, when paired with the appropriate spectacle lens and frame configuration.
Figure 3B:
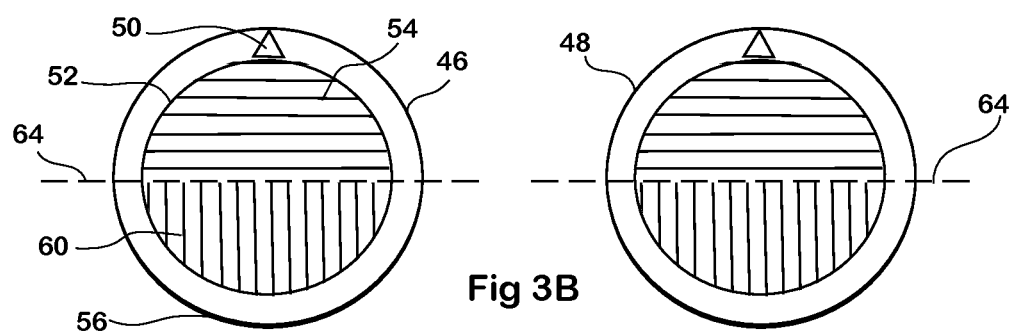
Figure 3C:
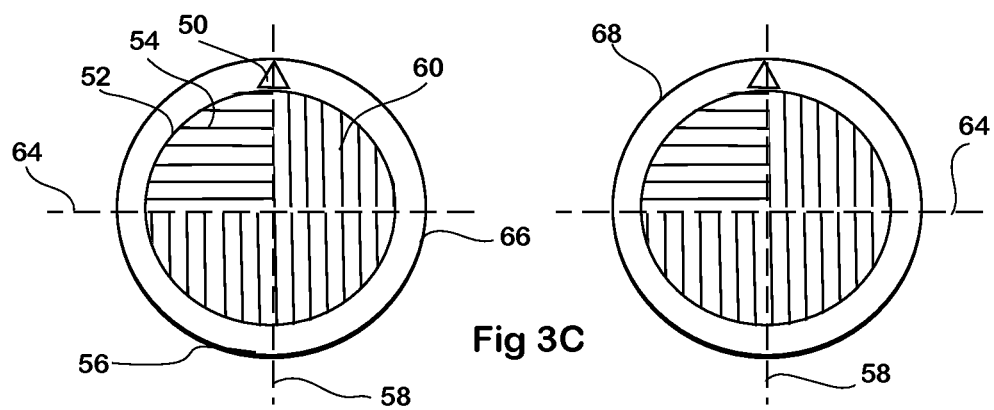

FIGS. 3A, 3B, and 3C depict a few of many embodiments of the contact lenses that can be utilized to simulate various visual field deficits. All of these lenses are viewed as if through the eyes of a human wearing the lenses, where the left lens is on the left eye and right lens is on the right eye. Additionally, a small demarcation 50 is present on the superior aspect of all the contact lenses to establish directionality and orientation. Rotational and positional stability are important to allow the contact lenses to track with eye movements and to also maintain the orientation of plane polarized regions of each contact lens. The contact lenses are rotationally stabilized by gravity through the use of denser material 56 at the bottom of each lens and they are positionally stabilized on the cornea of each eye by a contour change 52 on each lens that matches the natural topographical change that occurs as cornea transitions to sclera around the corneal limbus of the human eye. The outer scleral region 62 of each contact lens is located on the sclera of each eye and would thus not need to be made of polarizing or even transparent material, as light hitting that region is not directly involved in the perception of light.

In FIG. 3A the left contact lens 40 and the right contact lens 42 are identical and composed of two areas of orthogonally plane polarized material on either side of the vertical meridian 58 of each contact lens. The left sides of each contact lens have horizontal lines 54 that represent horizontal plane polarizing lens material, while the right sides of each contact lens have vertical lines 60 representing vertical plane polarizing lens material. When this pair of contact lenses are worn by a human user and used with spectacle lenses that linearly polarize light in the vertical plane, incident light subsequently travels through only the vertically plane polarized right visual fields of the contact lenses. This configuration simulates left homonymous hemianopia. If both the right and left spectacle lenses are rotated 90 degrees from the vertical meridian, they then linearly polarize light in the horizontal plane and thus only allow light to pass through the horizontally plane polarized left visual fields of the contact lenses. This configuration simulates right homonymous hemianopia. Alternatively, rotating the right spectacle lens horizontally and the left spectacle lens vertically can allow for the simulation of bitemporal hemianopia.

In FIG. 3B the left contact lens 46 and the right contact lens 48 are identical and composed of two areas of orthogonally plane polarized material on either side of the horizontal meridian 64. The superior visual fields of each contact lens linearly polarize light in the horizontal plane and are depicted with horizontal lines 54. The inferior visual fields of each contact lens linearly polarize light in the vertical plane and are depicted with vertical lines 60. When this pair of contact lenses are worn by a human user and used with spectacle lenses that linearly polarize light in the vertical plane, incident light subsequently travels through only the vertically plane polarized inferior visual field of the contact lenses. This configuration simulates superior homonymous hemianopia. If both right and left spectacle lenses are rotated 90 degrees from the vertical meridian, they then linearly polarize light in the horizontal plane and thus only allow light to pass through the horizontally plane polarized superior visual fields of the contact lenses. This configuration simulates inferior homonymous hemianopia.

In FIG. 3C the left contact lens 66 and the right contact lens 68 are identical and are composed of two areas of orthogonally plane polarizing material. The left superior quadrant of each contact lens is composed of horizontal plane polarizing material depicted with horizontal lines 54, while the remaining three quadrants of each contact lens are composed of vertically plane polarizing material depicted with vertical lines 60. The horizontal meridian is denoted with an imaginary dotted line 64, while the vertical meridian is denoted with an imaginary dotted line 58. When this pair of contact lenses are worn by a human user and used with spectacle lenses that linearly polarize light in the vertical plane, incident light subsequently travels through only the vertically plane polarized three quadrants of the contact lenses. This configuration simulates left superior homonymous quadrantanopia. Other visual field deficits can similarly be simulated by other embodiments of the invention that use contact lenses with orthogonal plane polarization regions in specific configurations.

Figure 4:
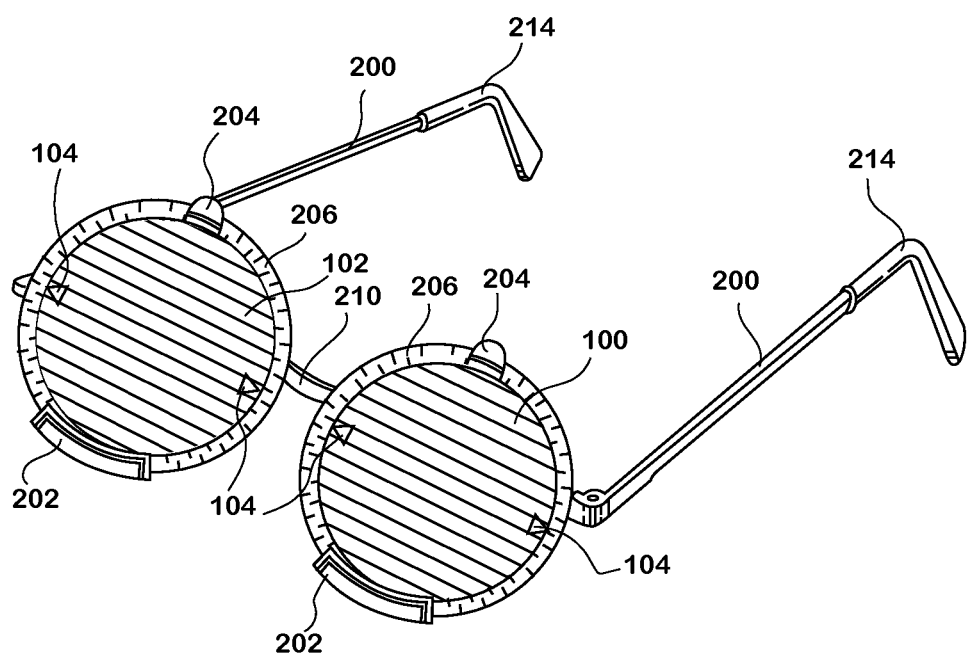
FIG. 4 shows plane polarized spectacle lenses within spectacle frames.

FIG. 4 depicts the left spectacle lens 100 and the right spectacle lens 102 housed within spectacle frames 200. The spectacle lenses are held in place within the circular rims of the spectacle frames by a bottom mounting bracket 202 and a top mounting bracket 204 in a loose manner that allows rotation of the spectacle lenses. The plane of polarization changes as the lenses rotate, thus necessitating a means of visualizing the degree of polarization. This is accomplished by two small triangular arrow knobs 104 on opposite ends of the spectacle lenses, which create an imaginary line between them that is parallel to the plane of polarization that the spectacle lens linearly polarizes light. The arrows are described as knobs because their three dimensional contour allows lateral pressure from a human finger to rotate the spectacle lens within its mounting brackets. Angle markings 206 on the rims of the glasses allow a user to know the degree to which the spectacle lenses are rotated by comparing the triangular arrow knobs 104 with the angle markings 206. The spectacle frames also consist of a nasal bridge 210 and temple tips 214 that allow for comfortable and stable positioning of the spectacle frame on said human wearer.

I claim:

1. An optical apparatus that simulates visual scotomas for basic and clinical research, and for diagnostic, prognostic, therapeutic, and commercial purposes, comprising:
   a. at least one spectacle lens that plane polarizes light and demarcates the directionality of polarization;
   b. a spectacle frame that allows said spectacle lens to rotate, wherein the degree that said spectacle lens is rotated from the vertical meridian is known and the plane of light polarization is also known by comparing the directionality of polarization demarcated on said spectacle lens with the degree of rotation indicated on said frame; and
   c. at least one contact lens, each with a plurality of areas that each polarize light in a different plane, wherein light that passes through said spectacle lens and subsequently through said contact lens is restricted from reaching specific areas of one or both retinas of a user, depending upon the angle differences between the planes of polarization of said spectacle lens and each plane of polarization within said contact lens.

2. The apparatus of claim 1 wherein said spectacle frame holds two of said spectacle lenses that can each be rotated independently to configure the plane of polarization of light passing through them to a precise degree of rotation from the vertical meridian of each lens, either congruently or incongruently from one another.

3. The apparatus of claim 2, wherein said contact lenses are comprised of two identical rotationally stabilized lenses each comprising two areas—one on either side of their vertical meridians—that plane polarize incident light in planes orthogonal to one another.

4. The apparatus of claim 2, wherein said contact lenses are comprised of two identical rotationally stabilized lenses, each comprising two areas—one on either side of their respective horizontal meridians—that linearly polarize incident light in planes orthogonal to one another.

5. The apparatus of claim 2, wherein said contact lenses are comprised of two mirror-image rotationally stabilized contact lenses, each comprising two areas—one on either side of their respective vertical meridians—that linearly polarize light in planes orthogonal to one another.

\* \* \* \* \*